United States Patent [19]

Day et al.

[11] Patent Number: 4,777,431

[45] Date of Patent: Oct. 11, 1988

[54] APPARATUS FOR MONITORING DIELECTRIC CHANGES IN POLYMERIC MATERIALS

[75] Inventors: David R. Day, Charlestown; Marvin L. Bromberg, Boston, both of Mass.

[73] Assignee: Micromet Instruments, Inc., Cambridge, Mass.

[21] Appl. No.: 879,322

[22] Filed: Jun. 27, 1986

[51] Int. Cl.[4] .............................................. G01N 25/66
[52] U.S. Cl. .................... 324/61 P; 324/65 P
[58] Field of Search ............... 324/61 R, 61 D, 62, 324/65 R, 65 P

[56] References Cited

U.S. PATENT DOCUMENTS

| | | | |
|---|---|---|---|
| 3,657,640 | 4/1972 | Jelinek et al. | 324/65 P |
| 3,857,284 | 12/1974 | Carron et al. | 324/61 N |
| 4,399,100 | 8/1983 | Zsolnay et al. | 422/62 |
| 4,423,371 | 12/1983 | Senturai et al. | 324/61 R |
| 4,496,697 | 1/1985 | Zsolnay et al. | 526/60 |

Primary Examiner—A. D. Pellinen
Assistant Examiner—Jeffrey A. Gaffin
Attorney, Agent, or Firm—Thomas J. Engellenner

[57] ABSTRACT

A dielectrometry apparatus for measuring the dielectric properties of a material, the apparatus including a casing adapted to be at least partially implanted into the material, the casing having a cavity defined by an opening which is capable of receiving a portion of the material upon implantation, a first electrode disposed within the cavity to make electrical contact with the material upon implantation, a second electrode disposed within the cavity in a spaced-apart relationship to the first electrode, the first and second electrode being adapted to make electrical contact with the material upon implantation, whereby dielectric measurements can be taken of the material in the cavity, a porous spacer for defining a fixed distance between the first and second electrodes and adapted for saturation with the material upon implantation, and a selectively permeable cover disposed across the opening of the cavity for permitting migration of the material upon implantation while excluding fillers that could interfere with the dielectric measurements.

25 Claims, 1 Drawing Sheet

APPARATUS FOR MONITORING DIELECTRIC CHANGES IN POLYMERIC MATERIALS

BACKGROUND OF THE INVENTION

The technical field of this invention is dielectrometry and, in particular, devices for sensing changes in the dielectric properties of materials undergoing state transitions such as resins undergoing curing.

It has become common for the manufacturers of parts molded from polymeric composites to employ on-line monitoring devices to measure the progress of curing. For example, parts of optimal density and strength can require careful control of the heat-up rate, temperature gradients within the part, the timing and amount of applied pressure and the cooling rate. In the past, control of these parameters has been conducted according to fixed schedules and often determined by trial-and-error methods.

A.C. measurements of dielectrical properties by sensors implanted within a curing polymer can provide useful data on curing and other material properties. In particular, U.S. Pat. No. 4,423,372 issued to Senturia et al in December, 1983 discloses that A.C. measurements in the frequency range of 1 Hz to 10 kHz can be reliable indicators of curing. See also U.S. Pat. No. 4,399,100 issued to Zsolnay et al in August, 1983 and U.S. Pat. No. 4,496,697 issued to Zsolnay et al in January, 1985 for further disclosures of automatic process control systems for curing polymeric materials.

Conventional sensors for measuring changes in the dielectric properties of a curing polymer are typically either formed as simple parallel plate capacitors, such as those disclosed in U.S. Pat. Nos. 4,399,100 or 4,496,697, or planar interdigitated capacitors such as those disclosed in U.S. Pat. No. 4,423,371. Unfortunately, these devices can be ill-suited for monitoring the dielectric properties of certain polymeric materials. For example, graphite-filled, polymeric resins, such as conductive polyimide and phenolic resins (e.g., PMR-15, LARC, and SKYBOND manufactured by Hexcell, U.S. Polymeric, Monsanto and others), often yield false dielectric measurements because the conductive components of the composite cause short circuits within the sensor. Conventional sensors also have a tendency to deteriorate in high temperature environments. Even when the sensor itself is not damaged by conductive particles, leakage currents can occur at high temperatures and degrade performance, thereby impairing the reproducibility and reliability of the dielectric measurements.

There exists a need for a more reliable, inexpensive, resin-cure sensor which is sensitive to dielectric property changes and which can be implanted during manufacture and be suitable for on-line testing. Preferably, the apparatus should be suitable for implantation in a wide variety of polymeric materials, including those which have conductive fillers.

SUMMARY OF THE INVENTION

An apparatus is disclosed which is particularly useful in measuring dielectric changes in materials, even when the conductivity of such materials would interfere with normal dielectric sensors. The device is especially well-suited for measuring changes in the dielectric properties of conductive particle-filled resins undergoing state transitions. The apparatus of the present invention is useful in monitoring curing parameters related to viscosity and glass transition etc., and thereby permitting feedback-controlled, curing protocols to be implemented during the manufacture of parts.

In one illustrated embodiment according to the present invention, a sensor is disclosed having a casing adapted to be at least partially implanted into the polymeric material and having a cavity capable of receiving a portion of the uncured polymer upon implantation. The casing serves to protect the electrical components of the sensor as well as provide a simple, unitary structure to house all the parts. Moreover, the casing and the components which it houses are designed to minimize leakage currents.

Within the casing, a first electrode is disposed to make electrical contact with the polymeric material upon implantation, and a second electrode is also disposed within the cavity in a spaced-apart relationship to the first electrode. In one illustrated embodiment, the second electrode is disposed between the first electrode and the opening of the cavity. The second electrode is permeable to the migration of the polymeric material into the cavity upon implantation and also adapted to make electrical contact with the material to take dielectric measurements in conjunction with the first electrode.

The reproducibility and reliability of the measurements are further insured by a porous spacer means disposed within the cavity between the first and second electrodes to define a fixed distance (and volume) therebetween. The sensor is adapted for saturation with the polymeric material upon implantation. A variety of porous spacer means can be employed including, for example, glass, quartz and ceramic ($Al_2O_3$, $AlSiO_4$, and $ZrO_2$) matrices.

The sensor can also include a resin-permeable cover disposed over the opening of the cavity when the dielectric properties of resins with conductive fillers are to be measured. The cover selectively permits migration of the polymeric material which excluding fillers that could interfere with dielectric measurements. For example, the cover material can be selected to be permeable to resin migration but not graphite fibers or particles. The cover material is typically less permeable than the spacer.

The invention will next be described in detail with reference to certain preferred embodiments. However, it should be clear to those skilled in the art that various additions, subtractions and modifications can be made without departing from the spirit or scope of the invention. For example, although the illustrated embodiments show the cover element and the second (porous) electrode as individual elements, the function of these components can be met by an electrode having as an integral part thereof, a selectively permeable cover. Moreover, it should be clear that although the casing is illustrated as being of unitary construction, it can also be manufactured in parts (e.g. an upper component and a lower component) and assemblied around the sensor electronics to provide the same protective function. Additionally, in particular applications it may be preferred to have more than two electrodes or electrodes of different sizes or shapes. In some applications, two flat plate electrodes can be used and the material to be monitored can be allowed to migrate into the sensor via side passageways thereby alleviating the need for a permeable second electrode.

DETAILED DESCRIPTION

Figure 1:
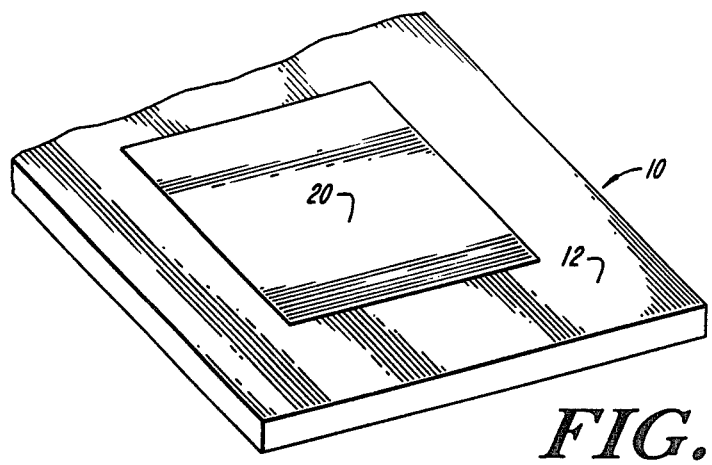
FIG. 1 is a partial schematic isometric view of the dielectrometry apparatus of the present invention.

In FIG. 1 an overall view of a sensor 10 according to the present invention is shown. The sensor includes a casing 12, preferably formed from Kapton (a polyimide material manufactured by the Dupont Company of Wilmington, Del.) or a similar high temperature-resistant material which is impervious to resin infiltration. Also shown in FIG. 1 is a cover 20 which is designed to act as a filter for the exlusion of conductive particles and fibers. The cover 20 serves to permit the material of interest (e.g., uncured resin) to enter a cavity beneath the cover while excluding conductive fillers which would otherwise interfere with dielectric measurements taken within the sensor 10. In use, the sensor is, at least, partially implanted or imbedded into the material to be tested so that the material can migrate through the cover 20 and fill the cavity.

Figure 2:
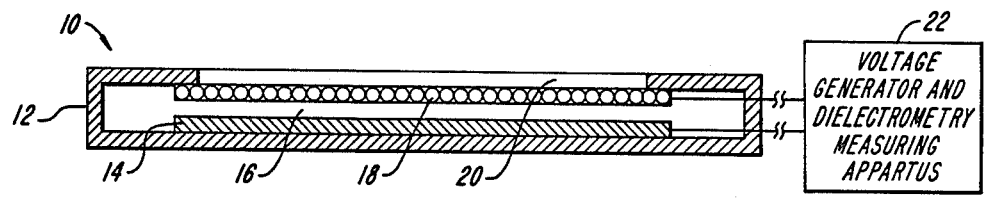
FIG. 2 is a schematic cross-sectional view of the apparatus of FIG. 1.

FIG. 2 is a cross sectional view of the sensor 10, showing the components which lie below the cover 12. As shown, the sensor 10 also includes a cavity in which a first electrode 14, a second electrode 18 and a porous spacer 16 are disposed. The spacer 16 is designed to be saturated with material to be tested and defines a fixed distance (and volume) between the first electrode 14 and the second electrode 18. The electrodes 14, 18 are adapted for electrical connection to a dielectrometry apparatus 22 for measuring changes in the dielectric properties of the material which enters the sensor 10.

Figure 3:
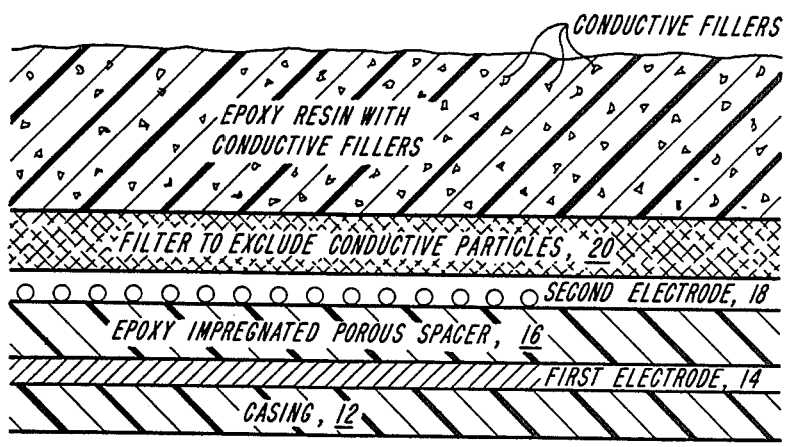
FIG. 3 is a more detailed cross-sectional view of the apparatus of FIG. 1.

The inner components of the sensor 10 are shown in more detail in FIG. 3, which illustrates the sensor 10 in use implanted within an epoxy resin with conductive filter materials. The first electrode 14 is preferably mounted to the casing 12 at the bottom of the cavity. This first electrode is preferably substantially planar and can be formed, for example, from a conductive metal, such as copper or silver. The porous spacer 16 is disposed above the first electrode 14 and is preferably formed from a porous, inert, matrix material such as a glass, quartz or ceramic material. Preferred materials for the porous spacer 16 include alumina, silica or zirconia felt materials or combinations of these materials, such as aluminum silicate felts. The second electrode 18 is disposed above the spacer 16 and is preferably formed from a substantially planar porous or mesh conductive material such as a copper or silver mesh. Also shown in FIG. 3, the cover 20 can be formed from the same or similar material to that of the spacer 16 (i.e. a porous ceramic felt or the like). When used to monitor the curing of graphite-filled polymers and the like, the cover 20 is preferably less permeable than the spacer 16 to insure that the conductive components are excluded from the cavity.

Various means can be used to connect the leads to the casing and assembly the casing, itself, when a two (or more) piece casing is employed. In particular, adhesives with low electrical conductivity at high temperatures are preferred when assembling sensors according to the present invention.

In use, the sensor can be implanted, for example, into a resin within a mold that will form a part upon curing. Preferably, the sensor 10 is implanted into a portion of the part which will trimmed off during subsequent finishing operations. Alternatively, the sensor 10 can be implanted into a region of part where it will not affect the strength and be allowed to remain imbedded in the finished part. Lead wires from the first and second electrodes 14, 18 are connected to dielectrometry measuring apparatus 22, such as the Eumetric (Reg. trademark) System II Microdielectrometer manufactured by Micromet Instruments, Inc. of Cambridge, Mass. A time-varying voltage (e.g. an A.C. signal) is applied to one electrode of the sensor and dielectric data are obtained by measuring the amplitude of the current and its phase relative to the input voltage at the second electrode.

What is claimed is:

1. A dielectrometry apparatus for measuring the dielectric properties of a material, the apparatus comprising:
   a casing having a cavity defined by an opening which is capable of receiving a portion of a material upon implantation of the casing into a material,
   a first electrode disposed within the cavity to make electrical contact with the material upon implantation,
   a second electrode disposed within the cavity in a spaced-apart relationship to the first electrode, the first and second electrodes being disposed to make electrical contact with the material upon implantation, whereby dielectric measurements can be taken of said material in the cavity, and
   porous spacer means for defining a fixed distance between said first and second electrodes and capable of saturation with the material upon implantation.

2. The apparatus of claim 1 wherein the apparatus further includes a selectively permeable cover means disposed across said opening of said cavity for permitting migration of the material upon implantation while excluding fillers that could interfere with said dielectric measurements.

3. The apparatus of claim 2 wherein the cover means is a porous material chosen from the group of glass, quartz and ceramic materials.

4. The apparatus of claim 2 wherein the cover means is a ceramic felt chosen from the group of alumina, silica and zirconia felts and combinations thereof.

5. The apparatus of claim 2 wherein the second electrode further comprises, as an integral part thereof, a selectively permeable cover means.

6. The apparatus of claim 1 wherein the material is a resinous polymer and the apparatus conducts dielectric measurements to monitor changes in the polymer during processing.

7. The apparatus of claim 1 wherein the first electrode is a substantially planar conductive metal material.

8. The apparatus of claim 1 wherein the second electrode is disposed within the cavity between the first electrode and the opening, and is permeable to migration of the material into the cavity upon implantation.

9. The apparatus of claim 8 wherein the second electrode is a substantially planar conductive mesh material.

10. The apparatus of claim 1 wherein the porous spacer means is a porous material chosen from the group of glass, quartz and ceramic materials.

11. The apparatus of claim 1 wherein the porous spacer means is a ceramic felt chosen from the group of alumina, silica and zirconia felts and combinations thereof.

12. The apparatus of claim 1 wherein the casing is a polyimide material.

13. A dielectrometry apparatus for measuring the dielectric properties of a material, the apparatus comprising:
- a casing having a cavity defined by an opening which is capable of receiving a portion of a material upon implantation of the casing into a material,
- a first electrode disposed within the cavity to make electrical contact with the material upon implantation,
- a second electrode disposed within the cavity in a spaced-apart relationship to the first electrode, the first and second electrodes being disposed to make electrical contact with the material upon implantation, whereby dielectric measurements can be taken of said material in the cavity,
- porous spacer means for defining a fixed distance between said first and second electrodes and capable of saturation with the material upon implantation, and
- a selectively permeable cover means disposed across said opening of said cavity for permitting migration of the material upon implantation while excluding fillers that could interfere with said dielectric measurements.

14. The apparatus of claim 13 wherein the first electrode is a substantially planar conductive metal material.

15. The apparatus of claim 13 wherein the second electrode is disposed within the cavity between the first electrode and the opening, and is permeable to migration of the material into the cavity upon implantation.

16. The apparatus of claim 15 wherein the second electrode is a substantially planar conductive mesh material.

17. The apparatus of claim 13 wherein the porous spacer means is a porous material chosen from the group of glass, quartz and ceramic materials.

18. The apparatus of claim 13 wherein the porous spacer means is a ceramic felt chosen from the group of alumina, silica and zirconia felts and combinations thereof.

19. The apparatus of claim 13 wherein the cover means is a porous material chosen from the group of glass, quartz and ceramic materials.

20. The apparatus of claim 13 wherein the cover means is a ceramic felt chosen from the group of alumina, silica and zirconia felts and combinations thereof.

21. The apparatus of claim 13 wherein the second electrode further comprises, as an integral part thereof, a selectively permeable cover means.

22. The apparatus of claim 13 wherein the casing is a polyimide material.

23. A method for measuring changes in the dielectric properties of a material, the method comprising:
- implanting a sensor within a material, the sensor having a casing and a cavity within the casing which is capable of receiving a portion of the material upon implantation, the cavity also containing a first electrode and a second electrode spaced apart from the first electrode, the electrodes being disposed to make electric contact with the material, and a porous spacer defining a fixed distance between the first and the second electrode,
- allowing the material to migrate into the cavity of the sensor and saturate the porous spacer, and
- applying a voltage to one of said electrodes and sensing a current at the other electrode, whereby changes in the impedance of the material disposed between said electrodes can be determined.

24. The method of claim 23 wherein the method further comprises employing a selectively porous cover means for covering the cavity of the sensor and excluding components of the material that would interfere with the dielectric measurements.

25. The method of claim 23 wherein the step of applying a voltage further includes applying a time-varing voltage.

* * * * *